United States Patent [19]

Stoddard

[11] Patent Number: 5,484,398
[45] Date of Patent: Jan. 16, 1996

[54] METHODS OF MAKING AND USING ULTRASONIC HANDPIECE

[75] Inventor: Robert B. Stoddard, Boulder, Colo.

[73] Assignee: Valleylab Inc., Boulder, Colo.

[21] Appl. No.: 210,787

[22] Filed: Mar. 17, 1994

[51] Int. Cl.⁶ ................................................ A61B 17/32
[52] U.S. Cl. ........................... 604/22; 601/2; 604/902; 433/119
[58] Field of Search ................. 604/22, 902; 601/2; 433/86, 91, 119

[56] References Cited

U.S. PATENT DOCUMENTS

| | | |
|---|---|---|
| 4,493,694 | 1/1985 | Wuchinich . |
| 4,516,398 | 5/1985 | Wuchinich . |
| 4,921,476 | 5/1990 | Wuchinich . |
| 5,076,276 | 12/1991 | Sakurai et al. ............... 602/2 |
| 5,151,083 | 9/1992 | Pichler ....................... 604/22 |
| 5,248,297 | 9/1993 | Takase ....................... 604/22 |
| 5,312,329 | 5/1994 | Beaty et al. ................. 604/22 |

*Primary Examiner*—Krista M. Zele
*Attorney, Agent, or Firm*—Peter C. Richardson; Lawrence C. Akers; Aaron Passman

[57] ABSTRACT

An ultrasonic surgical handpiece for surgery on a patient has a handpiece with distal and proximal ends on a housing thereof for manipulation by a surgeon. A vibrator is carried within a hollow inside of the housing. A tool extends from the vibrator at the distal end to a distal tip and is tubular with a bore along its axis so axial vibrations at high frequency are transmitted to the distal tip. Fluid flows from the distal tip to the vibrator, cools the vibrator and connects to a source of suction at the proximal end. A flue carried cantilever on the distal end extends about the tool so a space is between the tool and the flue for guiding fluid from the distal end to the distal tip. A port located through the tool connects between the space and the bore and is axially positioned near the distal end to collect fluid. An inlet on the flue is near the distal end for fluid provided by a supply. The inlet is axial distal of the port and/or may meter fluid to a preset range. The port may be at, near or toward a low stress region of the tool. The vibrator is piezo. The port can be diametrically opposed to the inlet. Holes may be located through the tool near the distal tip to prevent misting, clogging or dripping of fluid. A method of cooling the ultrasonic surgical handpiece has steps that circulate fluid from the inlet to the space and port and pass cooling fluid about the vibrator and to the source of suction. A method of making the ultrasonic tool may include having one or more ports through the tool to the bore wherein the ports are at, near or toward low stress regions and allow fluid flow from the space to the bore.

11 Claims, 3 Drawing Sheets

METHODS OF MAKING AND USING ULTRASONIC HANDPIECE

FIELD OF THE INVENTION

This relates to ultrasonic handpieces for surgical effects and more specifically to the cooling of the vibrator therein particularly during operation when clogged or semiclogged.

BACKGROUND OF THE DISCLOSURE

Ultrasonic surgical handpieces include a tool that is vibrated at ultra high frequency, i.e. over 23,000 cycles per second for generating a standing wave about a distal tip thereof. The energy produced and delivered at the distal tip effects cellular material of humans and animals by fragmentation and/or emulsification. Less substantial cells are destroyed initially such that selective surgical effects and procedures are possible. The distal tip is at an end of an elongate metal tubular tool that extends from the handpiece held by the surgeon. Fragmented and/or emulsified cellular debris can be removed from the operative site with suction applied to the treated tissue. Specifically, a passage through the tubular tool connects to a source of suction through which the debris is drawn. In piezo driven tools the passage continues through the vibrator and in magnetostrictive vibrators the passage runs parallel to the vibrator. With any vibrator the electrical energy supplied to generate the axial ultrasonic vibrations applied to the tool connected thereto has a portion of the electrical energy converted to heat. Heat is thus inevitably a part of the process and has been removed by a circulating coolant flow, air cooling, debris removed through the passage or any combination thereof, Depending upon the level of energy applied and the vibrator used, the type of cooling required varies and the techniques used are distinct. Some form of cooling remains necessary at all times during the operation of the vibrator to minimize its degradation due to the heat generated during conversion of electrical energy to ultrasonic vibrations useful for surgery. In ultrasonic surgical handpieces wherein the cooling is merely a result of fluid movement through the passage of the tool and vibrator, clogging and/or choked flow presents a serious concern to the proper and successful operation of the cooling system. That is to say that, in ultrasonic surgical handpieces wherein the removal of surgical debris is a means by which the heat energy generated by the vibrator is conducted away, a supplemental cooling circuit is required to prevent destruction of the vibrator. It makes no difference if the vibrator has piezo crystals or magnetostrictive laminations so long as the handpiece operating temperature is maintained at a low level comfortable to the surgeon.

Valleylab Inc, Boulder, Colo. manufactures ultrasonic surgical instruments and has a number of assigned patents. The present disclosure is also assigned to Valleylab Inc. Three patents held by Valleylab Inc are U.S. Pat. Nos. 4,493,694; 4,516,398 and 4,921,476 which disclose and claim ultrasonic surgical handpieces and methods including pre-aspiration holes located near the distal tip of the surgical tool. Those aforementioned patents teach the preaspiration device and its technique for use and more specifically the advantages of having preaspiration holes located near the distal tip of the tool. In the device disclosed therein an irrigation flue is carried to extend distally from the handpiece and surround the tool. The extending flue provides an annular space through which irrigant may flow toward the tip. It is thought in those patents that it is preferred to have the irrigant in fluid return through the preaspiration holes for these reasons. First is to prevent flooding the operating site with irrigation fluid such that the surgeon would have to deal with that in addition to the bodily fluids resulting from surgery. Second is to prevent misting resulting when the ultrasonic vibrations of the distal tip break up the irrigation fluid into five particles and disperse them there about as vapor. Third is the use of the irrigation fluid returned through the holes near the distal tip to lubricate, facilitate and promote the flow of debris removed from the operational site thereby preventing clogging. Because the irrigation fluid returned through the holes near the distal tip passes through the piezo vibrator with the debris, cooling is provided. For magnetostrictive a separate cooling loop is required. Piezo vibrators include a passage therethrough which allows the debris and irrigant to pass therethrough during removal for cooling. Consequently, the concept and execution of the preaspiration holes serve to permit an additional function of allowing added irrigation fluid flow for vibrator cooling during surgery but not when the tool is clogged and/or semi clogged.

Several problems exist when the preaspiration holes are placed near the distal tip including tool breakage. The tool is tubular titanium shaped with a Gaussian contour in side profile to resist the stresses and strains associated with being driven to vibrate at ultrasonic frequencies by the vibrator. That is to say that, the tubular titanium tool is stretched and compressed at over twenty thousand to forty cycles per second by the application of ultrasonic vibration. Consequently, discontinuities such as holes near the distal tip act as stress concentration. Unfortunately, those stress concentrations are disposed close to an area of maximum stress and present a problem. Specifically, and on occasion the distal tip of the tubular titanium tool will fracture circumferentially through the holes and drop off. That situation is unacceptable during a surgical procedure since the failure of the tool results in the distal tip falling directly into the operative site.

Wherein the aforementioned three advantages of the preaspiration holes are not essential or desired but cooling remains a concern the use of a circulating irrigation fluid flow sufficient to cool the vibrator remains a requirement for long life and cool operation. No existing ultrasonic surgical handpiece is available or known that has a vibrator cooling circuit through the tool and about the vibrator when the tip is clogged or semi-clogged.

SUMMARY OF THE INVENTION

An ultrasonic surgical handpiece provides surgical effects on a human or animal patient. A proximal end on the handpiece is manipulated by the surgeon. A housing is preferably shaped to be handheld and is hollow for enclosing ultrasonics. A tool may extend from a distal end of the housing to a distal tip thereof. A vibrator supported within the housing connects to the tool for transmitting thereto ultrasonic energy. An axis passes through the tool from the distal tip to the housing so that vibration of the tool maybe preferably axial, and at high frequency. A passage along the axis and through the tool cools the vibrator and provides fluid flow to the proximal end. A source of suction may connect near the proximal end for drawing fluid through the tool and for cooling the vibrator in the housing.

A flue is most preferably positioned about the tool and extends along the axis from the distal end toward the distal tip; the flue is carried cantilever by and sealed against the distal end. A space between the tool and the flue guides fluid from the distal end toward the distal tip. A port located through the tool may preferably connect between the space the passage. It is preferred that the port is axially positioned near the distal end of the handpiece for collection and return of fluid to cool the vibrator.

The flue near the distal end most preferably has an inlet for fluid that may be provided by a supply. The inlet is preferably positioned axially distal of the port. The vibrator may include piezo crystals responsive to ultrasonic high frequency electrical energy. The port preferably permits circulation of fluid in the range of 1 to 3 cubic centimeters per minute for cooling the piezo crystals. The port may be positioned axially along the tool toward a point of low stress.

The axis of the tool may be angled with respect to the vibrator so that the housing is angled relative to the tool. The port may preferably be diametrically opposed to the inlet. The flue and distal end are preferably configured for alignment to maintain the diametric opposition of the port and the flue. The port may be sized to control flow therethrough to the range of 1 to 3 cubic centimeters per minute. A pair of holes may additionally pass through the tool transverse to the axis and preferably near the distal tip and flue thereat. The pair of holes most preferably sized to be sufficient to pass fluid not returned through the port. The pair of holes passing fluid are preferably to minimize misting, clogging and dripping of excess fluid about the distal tip.

A method of cooling the ultrasonic surgical handpiece when performing ultrasonic surgery may have steps including handling and manipulating the housing of the ultrasonic surgical handpiece. A further step may be enclosing ultrasonics within the hollow inside of the handled housing. It is preferred to include a step of extending the tool from the distal end of the housing to the distal tip of the tool. Supporting the vibrator within the hollow and connecting the tool to the vibrator may be further steps that allow transmission of ultrasonic frequency energy through the tool. The step of transmitting vibrations axially along the tool between the distal tip and the vibrator may be a part of the method. It is preferred to flow fluid through the passage along the axis and from the distal tip to the vibrator. Extending the flue about the tool, from the distal tip to the distal and creating space therebetween is a step. Connecting a source of suction near the proximal end for drawing fluid through the tool and for cooling the vibrator is a method step. It is preferred to locate the port through the tool between the space and the passage so the port is axially positioned near the distal end for collecting fluid as a step of the method. Another step may include metering the flow of fluid to be maintained in the preferred range of 1 to 3 cubic centimeters per minute.

A method of making the ultrasonic tool for vibration along the axis thereof at high frequencies when driven by the vibrator into resonance may include the step of having the elongate tubular tool with a passage therethrough from the distal tip to the vibrator. The step of providing one or more ports through the tool from the passage to allow fluid flow into the passage when suction is applied thereto is preferred. The preferred method may include locating one or more of the ports near a low stress region thereat while allowing fluid flow therethrough.

DETAILED DESCRIPTION OF THE INVENTION

Figure 1:
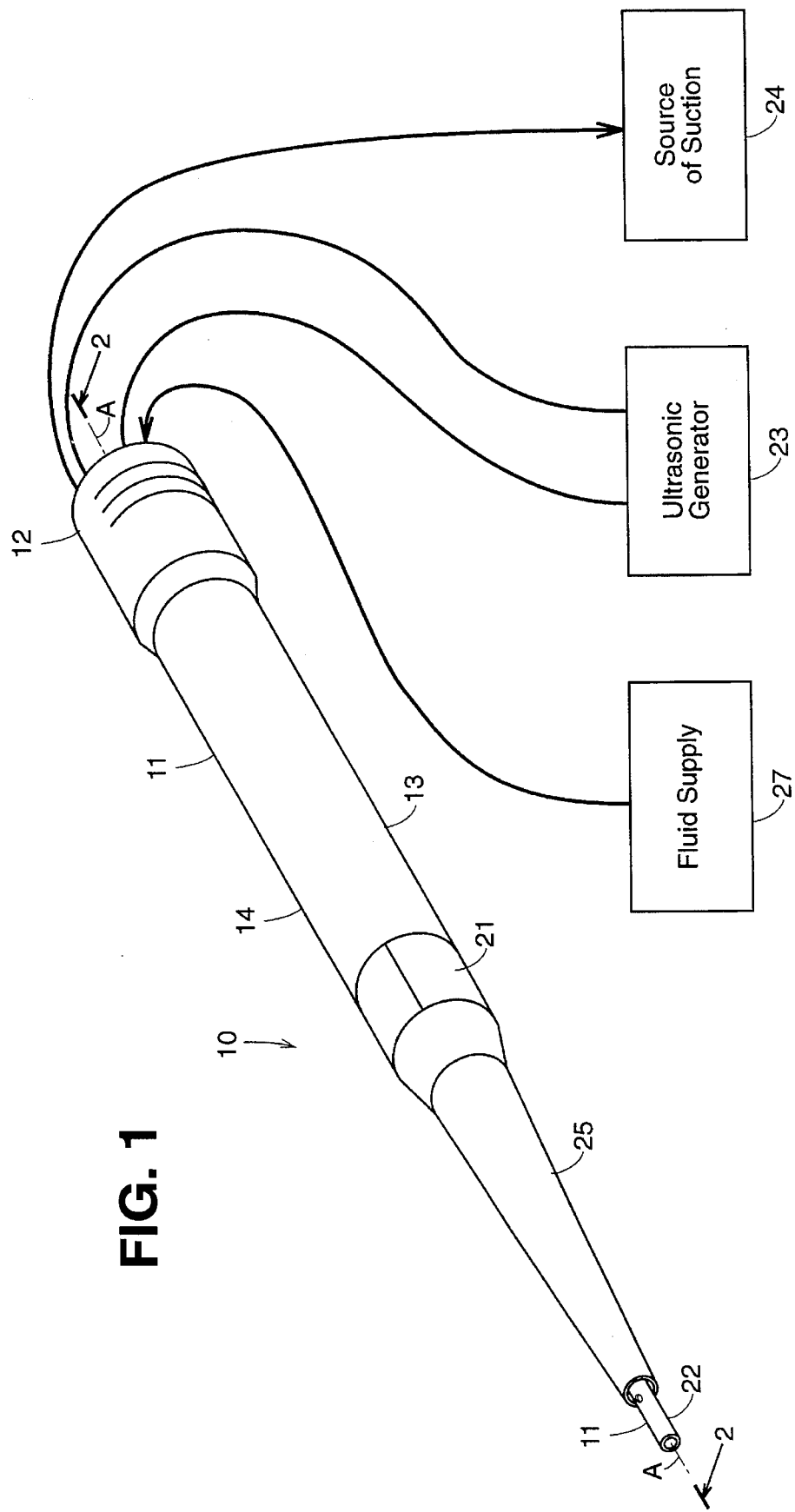
FIG. 1 is a perspective view shown schematically of the ultrasonic surgical handpiece connected to a generator and a source of suction and a supply of fluid.

An ultrasonic surgical handpiece 10 for surgical effects on a patient either human or animal includes an elongate handpiece 11 shaped to be handheld by a surgeon. The handpiece 11 has a proximal end 12 away from the patient but for manipulation by the surgeon during ultrasonic emulsification by the generating wave forms that excite cellular material and/or liquid thereabout to fragment and/or emulsify tissue and bodily fluids for removal as desired. Consequently, the ultrasonic surgical instrument 10 can be operated to selectively surgically remove unwanted tissue. The preferred ultrasonic frequency is at about 23,000 cycles per second for neuro, hepatic and other procedures requiring separation of tissue from vasculature.

A housing 13 molded of polymeric material and shaped to include a grip 14 on its outside and a hollow 15 in its inside encloses ultrasonics therewithin. A tool 16, preferably tubular, hollow and titanium has a passage or bore 17 along an axis "A" thereof. The tool 16 has a Gaussian profile to minimize stress. Specifically, the tool 16 vibrates axially expanding and contracting at a resonant frequency to which it is tuned whereby the stress profile wave form as illustrated at 18 in FIG. 2 exists along the tool 16.

Figure 2A:
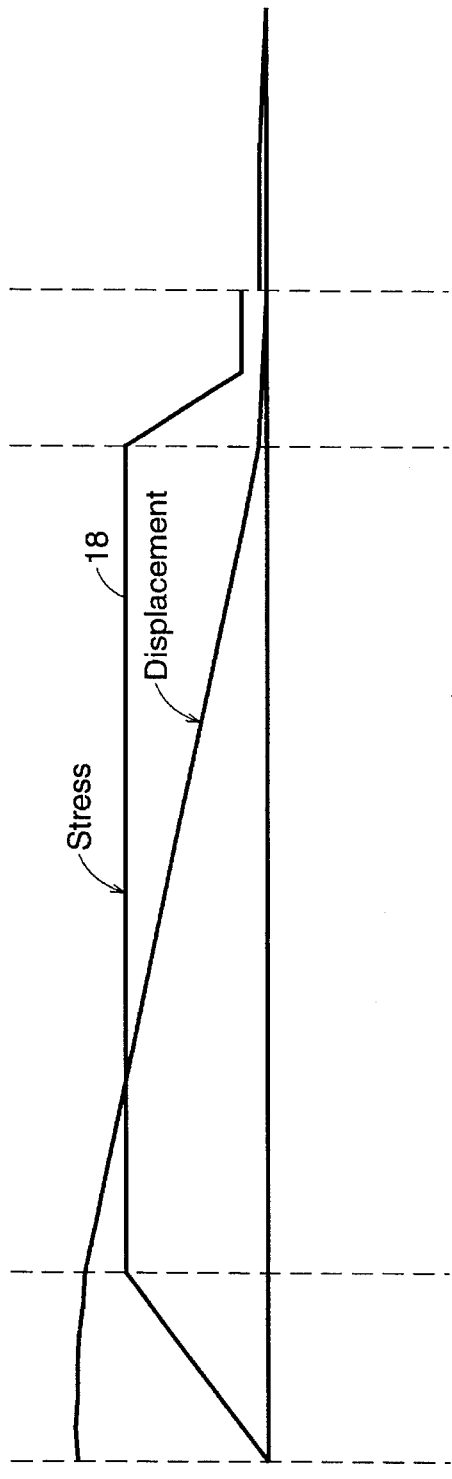
FIG. 2 is a side view in cross section of the ultrasonic surgical handpiece as would be seen along line 2—2 of FIG. 1 if the vibrator therein were piezo.
Figure 2B:
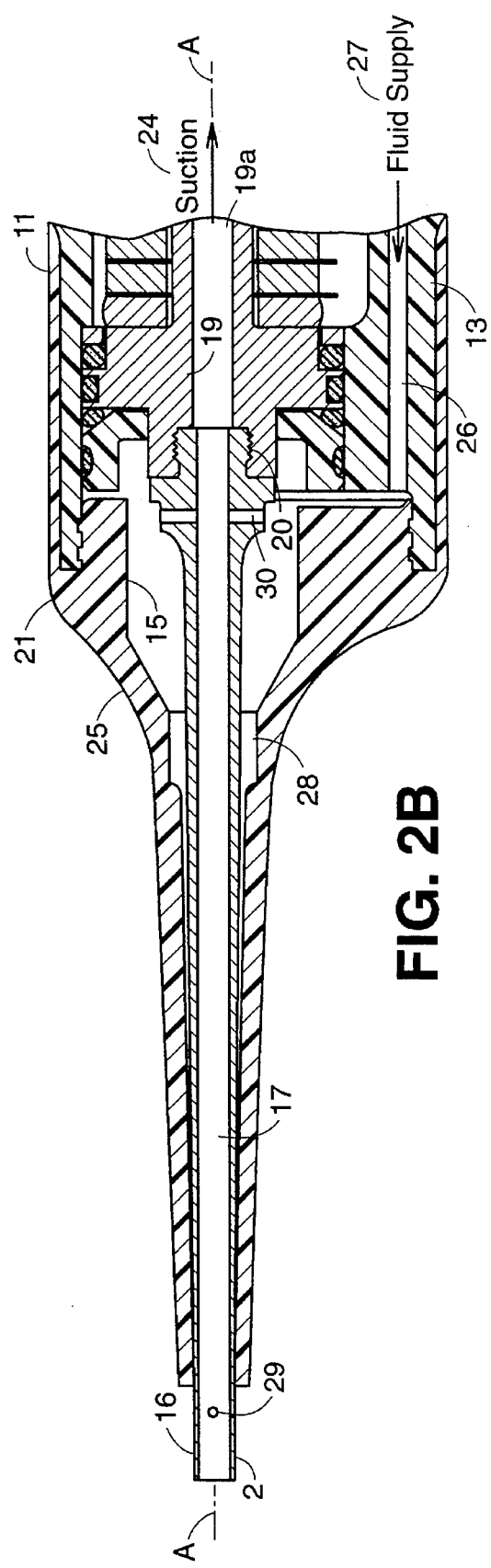

A vibrator 19 is carried with the hollow 15 of the housing 13 and in particular as shown in cross section in FIG. 2. The vibrator 19 may be piezo crystals. The vibrator 19 has a threaded connection 20 to facilitate removably attaching the tool 16 to the vibrator 19 near a distal end 21 of the handpiece 11. The tool 16 extends away from the distal end 21 along the axis "A" and is of a length measured in wave lengths or fractions thereof so that a distal tip 22 of the tool 16 has the maximum elongations and contractions necessary for the best surgical effects to fragment, emulsify or destroy tissue. To remove surgically altered tissue the bore 17 provides a convenient and useful corridor for debris.

Near the distal end 21 the bore terminates at the vibrator 19 and the corridor for the debris continues being plumbed through the vibrator 19 to provide cooling. Specifically, only 75 to 85 percent of the electrical high frequency energy provided by a generator 23, in FIG. 1 is converted to ultrasonic resonant vibration by the vibrator 19; the rest becomes heat that must be removed. Cooling for the vibrator 19 is effective to eliminate this unwanted heat. In the ultrasonic surgical handpiece 10 wherein the vibrator 19 includes a piezo crystal there can be a centered opening 19a therethrough and connected directly in line with the bore 17. The debris is thus passed right through that vibrator 19 as shown in FIG. 2 and heat is removed in the process.

Since the invention of this disclosure is not specifically the plumbing used to cool the vibrator 19 and the details thereof are not relied upon to support the claims, the exact arrangement for cooling is not essential. Skilled artisans will no doubt understand that the cooling required demands thermal intimacy between the vibrator 19 and the fluid and debris removed from the operational site.

A source of suction 24 in FIGS. 1 and 2 is provided at the proximal end 12 to connect through the housing 13 for drawing fluid and debris for the cooling of the vibrator 19. That is to say that, the source of suction 24 pulls the fragmented and emulsified cellular matter, tissue and fluids through bore 17 and through or about the vibrator 19 so that it may exit at the proximal end 12. The source of suction 24 is shown as a block in FIG. 1 but may be any pump capable of drawing a vacuum. It is preferred that a high volume pump be used that is self priming. Hospital wall suction to a central vacuum is also a possible source of suction 24. A canister can be interposed between the proximal end 12 and the source of suction 24 to trap the fluid and debris for disposal or analysis as desired.

A flue 25, shown in FIGS. 1 and 2, is positioned about the tool 16 and extends along axis "A" from the distal end 21 toward the distal tip 22. The flue 25 is preferably of a resilient, soft polymer material such as silicone rubber and is coaxially carried about but separate from the tool 16. To that end, the flue 25 is supported at the distal end 21 and is conjugate with respect to the housing 13. Different ways of attaching the flue 25 to the housing 13 include threads, press fit about: and the like are possible. Consequently, and as shown in the FIGS. 1 and 2, the flue 25 is enlarged to be placed over the distal end 21 and thus may be sealed thereto forming a removable fluid tight connection thereabout. The flue 25 and distal end 21 can be configured to interengage one another at a specific orientation so that the relationship both axial and rotary are always the same. With regard to the axial relationship it is preferred that the distal tip 22 always extend beyond the flue 25. Concerning rotary relative relationship, there is an inlet 26 connected to the flue 25 and located in the enlarged part thereof near the distal end 21, see FIG. 2. Inlet 26 is positioned as shown inside the flue 25 in FIG. 2 so that it may be conveniently connected to a supply of fluid 27. The fluid from the supply of fluid 27 can be any irrigant and/or anticoagulant. The purpose of the fluid is disclosed in U.S. Pat. Nos. 4,063,557, 4,493,694; 4,516,398 and 4,921,476 which are incorporated herein and made a part hereof by reference. Briefly, the fluid is introduced into the flue 25 through the inlet 26 and passes along the tool 16. More specifically, an annular space 28 between the flue 25 and the tool 16 reaches from the distal end 21 almost to the distal tip 22 in the preferred embodiment, see FIG. 2 for example. The distal tip 22 extends beyond the flue 25 about 4 to 6 millimeters.

The fluid passing down the annular space 28 will reach the distal tip 22 and be vaporized by the ultrasonic vibrations of the tool 16, or will drip off the distal tip 22 into the operation site. If the teachings of the referenced patents are followed, then holes 29 located near the distal tip 22 pass through the tool 16 adjacent the flue 25 thereabout. Those holes 29 act to capture excess fluid passing through the annular space 28 and prevent or minimize vaporization (misting at the distal tip 22), dripping and/or clogging in the bore 17.

With regard to clogging, the return of fluid through the holes 29 and up the bore 17 acts to lubricate debris and fluid removed from the operative site whereby clogging is minimized or eliminated. When the source of suction 24, draws the debris and fluid up the bore 17 about or through the vibrator 19 and out the proximal end 12. The fluid from the supply of fluid 27 will therefore act to aid in cooling the vibrator 19 in addition to the removed debris, tissue and emulsified material of the patient.

It is preferred that one or more ports 30, see FIG. 2, be provided with each extending from the annular space 28 to the bore 17 to permit passage of fluid from the supply of fluid 27 to the source of suction 24. An embodiment is shown in FIG. 2 wherein ports 30 located axially proximal of the inlet 26 and may be diametrically opposed thereto. During an ultrasonic surgical procedure it is desired to establish a wave front beyond the distal tip 22 which acts to fragment, destroy and/or emulsify patients tissue and/or cellular matter. If however, the surgeon places the distal tip 22 directly against the tissue closing off the flow of fluid therethrough and if there are no holes 29 to remove excess fluid from the annular space 28 or the holes are clogged by tissue and/or debris then one or more ports 30 permit and encourage fluid flow therethrough for cooling the vibrator 19 during such choked operation. While only one port 30 may be preferred and adequate to bypass the typical circulation during clogged or choked conditions it is also possible to provide additional ports 30. The criteria is to keep at least a minimum fluid flow in the range of 1 of 10 cubic centimeters per minute adequate for cooling the vibrator 19. The one or more ports 30 thus act as a metering system capable of always supplying at least the minimum fluid flow necessary for cooling vibrator 19 no matter what has happened at the distal tip 22 and/or the holes 29, if included. As an alternative, the port 30 may be located distally in vibrator 19 as also shown in FIG. 2.

The tool 16 is under a great deal of stress due to being driven into ultrasonic resonance by the vibrator 19 and so it is preferred that one or more ports 30 be located near low stress regions on the tool 16. The wave form 18 shown above the tool 16 in FIG. 1 represents the stress amplitude at each axial location along the tool 16. The concept of placing the ports 30 at, near or toward nodes when possible is to minimize the effect for stress contraction due to removal of material from the tool 16 when a port 30 is made.

Figure 3:
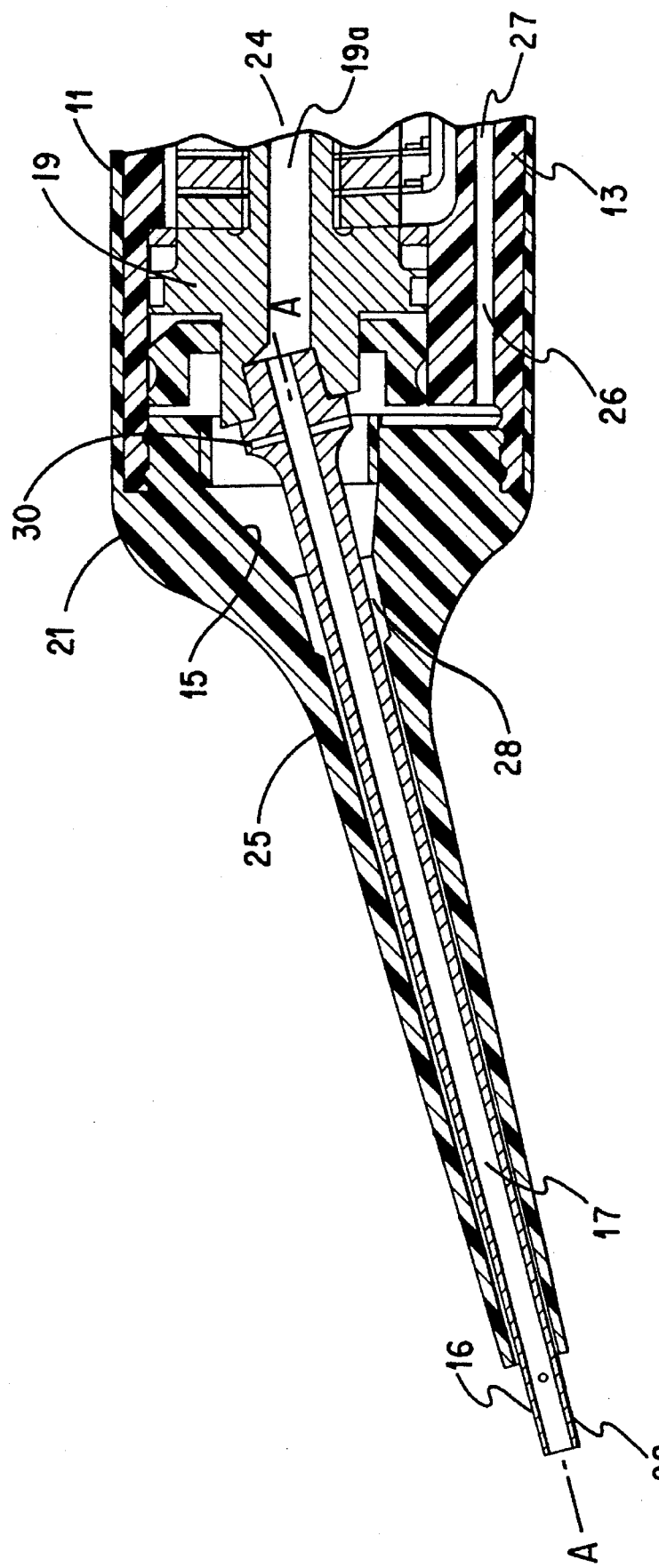
FIG. 3 is a side view in cross section of the ultrasonic surgical handpiece similar to FIG. 2 but wherein the tool axis is at an angle to the housing for the vibrator.

As shown in FIG. 3, the axis "A" may be at an angle relative to the vibrator 19 to provide an ergonomic position of the housing 13 relative to the distal tip 22 of the tool 16. The angularity of the axis "A" to the housing 13 permits the placement of the distal tip 22 while holding the housing 13 comfortably due to minimizing the bending of the surgeon's wrist. U.S. Pat. Nos. 4,747,820; 4,846,790 and 4,881,761 generally teach angularity and are incorporated herein by reference.

A method of cooling the vibrator 19 and therefore the housing 13 for performing ultrasonic surgery while handling and manipulating the housing 13 to control the position of the distal tip 22 of the tool 16 extending from the distal end 21 has steps. Supporting the vibrator 19 within the housing 13 and removably connecting the tool 16 to the vibrator 19 is a step which allows transmission of vibrations along tool axis "A" to the distal tip 22. A further step includes passing fluid through the bore 17 from the distal tip 22 to the vibrator 19. Extending the flue 25 about the tool 16 from the distal tip 22 to the distal end 21 is a step that creates the annular space 28. Connecting the source of suction 24 near the proximal end 12 draws the fluid from the bore 17 and through the vibrator 19 to thereby cool the vibrator 19. Locating one or more ports 30 near the distal end 21 and through the tool 16 or vibrator 19 for connecting the bore 17 with the inlet 26 acts to bypass the fluid flow under clogged or choked conditions near the distal tip 22. Consequently, at least some fluid is metered to the vibrator 19 for cooling.

What is claimed is:

1. An ultrasonic surgical handpiece for providing surgical effects at an operational site on a patient comprising:

a handpiece having a proximal end for handling and manipulation by a surgeon, the handpiece having a distal end;

a housing of the handpiece shaped to be handheld, the housing having a hollow for enclosing ultrasonics;

a tool extending from the distal end of the handpiece;

a distal tip on the tool away from the distal end;

a vibrator supported within the hollow of the housing and connected to the tool for transmitting thereto ultrasonic frequency energy, the vibrator having an opening;

an axis passing through the tool along which axial vibration at high frequencies are transmitted;

a tool bore extending along the axis through the tool to carry debris and fluid through the vibrator opening and for cooling the vibrator while providing fluid flow from the distal tip to the proximal end;

a source of suction connected to the proximal end for drawing fluid through the tool bore and the vibrator opening for cooling the vibrator in the housing;

a flue positioned about the tool and extending along the axis from the distal end toward the distal tip, the flue carried cantilever and sealed against the distal end;

a source of fluid connected to the distal end;

a space between the tool and the flue for guiding fluid from the distal end toward the distal tip, and a tool port extending from the space to the bore to permit passage of fluid from the source of fluid to the source of suction, the tool port located near low stress regions of suction, the tool port near nodes of the tool to minimize the effect of stress concentration due to removal of material from the tool through the tool port, the tool port axially positioned near the distal end for collection of fluid for cooling the vibrator so that there is thermal intimacy between the vibrator and the fluid and debris removed from the operational site.

2. The ultrasonic surgical handpiece of claim 1 wherein the flue near the distal end has an inlet for fluid provided by the source of fluid.

3. The ultrasonic surgical handpiece of claim 2 wherein the inlet is axially distal of the opening of the vibrator.

4. The ultrasonic surgical handpiece of the claim 3 wherein the vibrator includes a piezo crystal responsive to ultrasonic high frequency electrical energy.

5. The ultrasonic surgical handpiece of the claim 4 wherein the tool port has means for circulating the fluid in the range of 1 to 10 cubic centimeters per minute for cooling the piezo crystal.

6. The ultrasonic surgical handpiece of the claim 2 wherein there is only one tool port located diametrically opposite to the inlet, and the configurations of the flue and distal end when assembled align and maintain the tool port diametrically opposite the flue.

7. The ultrasonic surgical handpiece of the claim 1 wherein the axis of the tool is angled with respect to the vibrator so the housing has an angle relative to the tool axis.

8. The ultrasonic surgical handpiece of the claim 1 wherein the tool port has means for controlling flow of the fluid that is sized to control flow therethrough to the range of 1 to 10 cubic centimeters per minute.

9. The ultrasonic surgical handpiece of the claim 1 wherein a pair of holes pass through the tool near its distal tip, the pair of holes sized to be sufficient to pass fluid not returned through the tool port in an amount sufficient to minimize misting, clogging or dripping of excess fluid about the distal tip.

10. A method of cooling an ultrasonic surgical handpiece when performing ultrasonic surgery including the steps of:

handling and manipulating a hollow housing of an ultrasonic surgical handpiece near a proximal end thereof;

extending a tool from a distal end of the housing;

supporting a vibrator within the hollow housing and connecting the tool to the vibrator for transmitting ultrasonic frequency energy through the tool;

transmitting vibrations through the tool along an axis thereof between the vibrator and a distal tip;

flowing fluid through a bore of the tool along the axis from the distal tip to and through an opening of the vibrator;

extending a flue about the tool from the distal end toward the distal tip to create a space therebetween;

connecting a source of suction near the proximal end for drawing fluid through the tool bore and the opening of the vibrator for cooling the vibrator;

providing a fluid supply at the distal end, and locating a tool port near the distal end and in a low stress area of the tool between the space and a bore so the tool port is axially positioned near the distal end for cooling the vibrator even when the tool bore is clogged.

11. The method of claim 10 having the added step of using the tool port to meter the flow of fluid to be in the range of about 1 to 10 cubic centimeters per minute.

* * * * *